United States Patent [19]

Bencsits

[11] Patent Number: 5,591,727

[45] Date of Patent: Jan. 7, 1997

[54] INSECTICIDAL COMPOSITION

[75] Inventor: Franz Bencsits, Wehrenbachhalde 54, 8053 Zürich, Switzerland

[73] Assignees: Perycut-Chemie AG; Franz Bencsits, both of Switzerland

[21] Appl. No.: 386,126

[22] Filed: Feb. 7, 1995

Related U.S. Application Data

[63] Continuation of Ser. No. 988,922, filed as PCT/EP91/01735, Aug. 4, 1992, abandoned.

[30] Foreign Application Priority Data

Sep. 12, 1990 [DE] Germany .................... 901300 U

[51] Int. Cl.$^6$ .................... A01N 65/00; A01N 53/02; A01N 53/04; A01N 53/10
[52] U.S. Cl. ................ 514/68; 514/65; 514/66; 514/67; 514/69; 514/70; 514/71; 514/72; 514/73; 514/74; 514/421; 514/444; 514/445; 514/461; 514/519; 514/520; 514/521; 514/523; 514/525; 514/530; 514/531; 514/547; 514/567; 514/970; 514/972; 424/195.1
[58] Field of Search ................ 514/65, 70, 72, 514/547, 567, 66–69, 71, 73–74, 421, 444, 445, 461, 519–521, 523, 525, 530, 531, 970, 972; 424/195.1

[56] References Cited

U.S. PATENT DOCUMENTS

| | | | |
|---|---|---|---|
| 2,377,029 | 5/1945 | Norris .................... | 426/544 |
| 2,383,815 | 8/1945 | Riemenschneider et al. ........ | 554/3 |
| 2,485,640 | 10/1949 | Vahlteich et al. ............. | 426/545 |
| 3,560,613 | 2/1971 | Miskus et al. ............... | 514/68 |
| 4,125,400 | 11/1978 | Downer et al. .............. | 514/772 |
| 4,320,139 | 3/1982 | Takei ..................... | 514/461 |
| 4,668,666 | 5/1987 | Allan et al. ................ | 514/63 |
| 4,674,445 | 6/1987 | Cannelongo ............... | 119/156 |
| 4,683,132 | 7/1987 | Ronning et al. ............. | 424/409 |
| 4,923,745 | 5/1990 | Wolfert et al. .............. | 428/354 |
| 5,102,662 | 4/1992 | Gallagher ................. | 424/409 |
| 5,334,585 | 8/1994 | Derian et al. ............... | 514/74 |

FOREIGN PATENT DOCUMENTS

| | | |
|---|---|---|
| 147947 | 7/1985 | European Pat. Off. . |
| 2375826 | 7/1978 | France . |
| 2615646 | 10/1976 | Germany . |
| 625683 | 7/1949 | United Kingdom . |
| 1013946 | 12/1965 | United Kingdom . |
| 2002635 | 7/1978 | United Kingdom . |
| 2058569 | 4/1981 | United Kingdom . |
| WO86/03374 | 6/1986 | WIPO . |

OTHER PUBLICATIONS

Food Science and Technology Abstracts (FSTA) 85: 973; Abstracting, Kanematsu et al., "Studies on the improvement of antioxidant effect of Tocopherols . . ." Yukagaku, vol. 32(12), 1983, pp. 731–734.

Rompps Chemie–Lexikon, 8th edition (1987), pp. 3413–3414.

"Stabilization of Thin Films of Pyrethrins and Allethrin", J. Agr. Food Chem., vol. 20, No. 2 (1972), p. 315.

Stabilization of Thin Films of Pyrethrins and Allethrin, Miskus et al., Pyrethrum Post, 11(4):135–137 (1972).

Primary Examiner—John Pak
Attorney, Agent, or Firm—Finnegan, Henderson, Farabow, Garrett & Dunner, L.L.P.

[57] ABSTRACT

The invention relates to an insecticidal composition which comprises at least one pyrethroid, at least one UV absorbing agent and at least one antioxidant from the group consisting of tocopherol derivatives and citric acid esters. This insecticidal composition can in particular be used as an emulsion or on a powdery carrier for the control of flying and crawling insects such as flies and cockroaches.

16 Claims, 1 Drawing Sheet

INSECTICIDAL COMPOSITION

This application is a continuation of application Ser. No. 07/988,922, filed as PCT/EP91/01735, aug. 4, 1992, now abandoned.

BACKGROUND OF THE INVENTION

The present invention relates to an insecticidal composition comprising an active amount of at least one pyrethroid, at least one UV absorbing agent and at least one antioxidant, and its use for controlling flying and crawling insects.

The insecticidally effective components of pyrethrum and its synthetic analogues, which are derived from the structure indicated in the following, are designated as pyrethroids. The main active substances in pyrethrum are the cinerins I and II, the pyrethrins I and II and the jasmolins I and II (R ömpps Chemie-Lexikon, 8th edition (1987), page 3413).

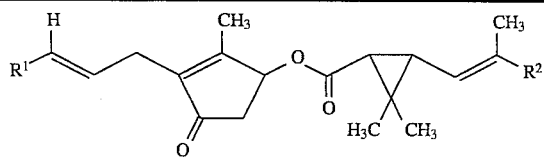

| | |
|---|---|
| Pyrethrin I: | $R^1 = CH=CH_2, R^2 = CH_3$ |
| Pyrethrin II: | $R^1 = CH=CH_2, R^2 = COOCH_3$ |
| Cinerin I: | $R^1 = R^2 = CH_3$ |
| Cinerin II: | $R^1 = CH_3, R^2 = COOCH_3$ |
| Jasmolin I: | $R^1 = C_2H_5, R^2 = CH_3$ |
| Jasmolin II: | $R^1 = C_2H_5, R^2 = COOCH_3$ |
| Allethrin: | $R^1 = H, R^2 = CH_3$ |

Pyrethrum is obtained from the dried flower heads of various pyrethrum or chrysanthemum species by pulverization or extraction and contains as main active substances pyrethroids such as pyrethrins, cinerins and jasmolins. Apart from nicotine, pyrethrum is the strongest vegetable insecticide; however, its effectiveness is reduced by sunlight and heat (Römpps Chemie-Lexikon, 8th edition (1987), page 3414). The lack of stability, but also the high price of natural pyrethroids led to the development of numerous synthetic derivatives.

Pyrethroids are generally used as isomer mixtures. They have been used for a long time as insecticides, in particular against common houseflies, cockroaches or blackbeetles and other household vermin, moths, corn weevils, mosquitoes, garden and greenhouse parasites, hay worms in viticulture and boll-weevils. Particularly, the natural pyrethroids distinguish themselves by a rapid so-called knock-down effect, i.e. the insects are certainly paralyzed rapidly, but only temporarily, and they recover again. The oxidative detoxication metabolism of the insects is responsible for this undesired effect.

Due to the great instability of the pyrethroids to air and light, numerous attempts have already been made to stabilize pyrethroids and to prolong their effectiveness.

Pyrethrum Post 11(4), 135–7, 51 and J. Agr. Food Chem. 20(2), 313–15 disclose the stabilizing of pyrethrins and allethrin by the addition of an antioxidant and a UV absorbing agent in a mineral oil formulation. While non-stabilized formulations are destroyed almost completely within 4 hours, the combination of an oxidant and a UV absorbing agent results in a considerable stabilization of the pyrethroids for at least 4 hours and more.

Aromatic ketones in which two aromatic rings are directly bonded to an oxo group, e.g. benzophenone derivatives, and esters of aromatic acids, such as esters of substituted benzoic acids are mentioned. The used antioxidants have an OH group, which is directly bonded to an aromatic ring, and at least 14 carbon atoms such as 4-methyl-2,6-di-tert.-butyl phenol or 2,6-dioctadecyl-p-cresol.

US-A-3-506-613, WO-A-86/03374, EP-A-147 947, DE-A-2 615 646 and GB-A-2 058 569 describe various insecticidal compositions on pyrethroid basis, which contain antioxidants and customary UV absorbing agents for stabilizing the pyrethroids. 2,6-di-tert.-butyl-4-methyl phenol, 2,6-dioctadecyl-p-cresol, butylated hydroxy toluene, alkylated phenols, tert.-butyl hydroquinone, butylated hydroxy anisoles, ethoxy chin, ascorbic acid, their salts and derivatives and propionic acid salts are used as antioxidants. However, the stability of these compositions is not satisfactory.

It is the object of the present invention to provide an insecticidal composition with improved long-term effect.

SUMMARY OF THE INVENTION

This object is solved by an insecticidal composition of the type mentioned above, which is characterized in that the contained antioxidant is at least one citric acid ester.

DESCRIPTION OF PREFERRED EMBODIMENTS

Figure 1:
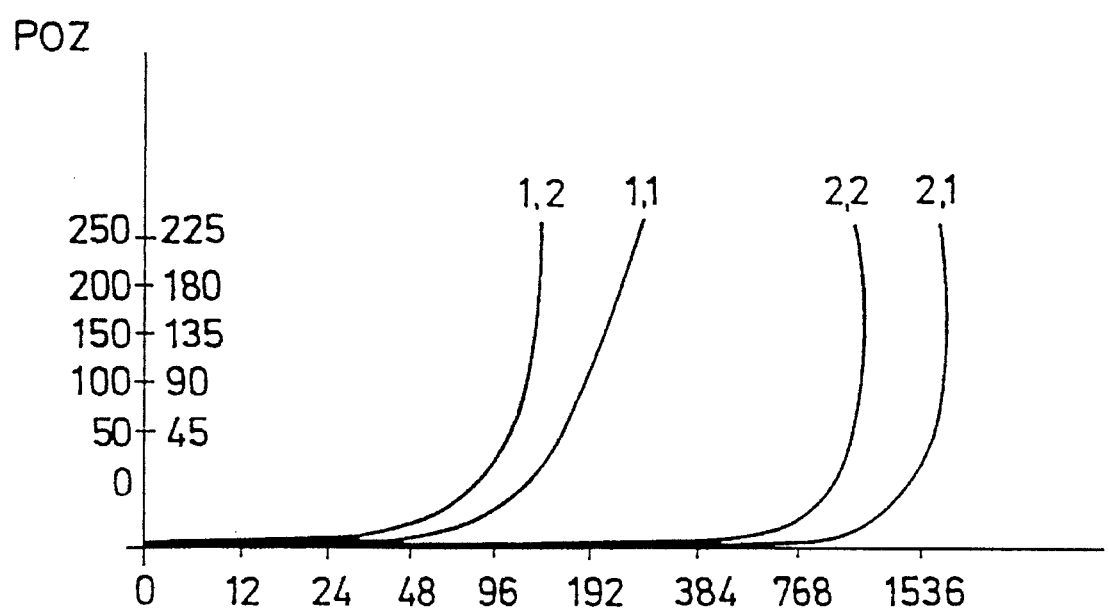
FIG. 1 is a plot of peroxide numbers and conductivities for various insecticide compositions versus time.

The composition according to the invention is suited for the control of vermin such as household vermin, in particular flies and cockroaches or blackbeetles.

The insecticidal composition has surprisingly a greatly improved long-term effect against vermin due to its high stability to UV light and/or its resistance to oxidation. The sensistivity of the composition to UV light is attributable to an oxidation of the free fatty acids, an autoxidation by a chemical reaction of air oxygen with the double bonds contained in unsaturated fatty acids being also possible. This sensitivity is drastically reduced according to the invention by the use of citric acid esters as an antioxidant. Ascorbyl palmitate may be contained as a further antioxidant.

The citric acid esters are preferably mono- to tri-esters of citric acid with alkyl alcohols having 1 to 8 carbon atoms.

The antioxidant is used in the composition used according to the invention preferably in an amount of 0.001 to 10% by weight, especially preferred of 0.01 to 5% by weight, in particular of 0.03% by weight, based on the composition.

All natural and synthetic pyrethroids, either alone or in mixture, can be used in the insecticidal composition used according to the invention. Natural pyrethrum proved to be especially effective.

The pyrethroid is preferably used in an amount of 0.001 to 10% by weight, especially preferred of 0.01 to 2% by weight, in particular of 0.03% by weight, based on the composition.

UV absorbing agents used according to the invention are generally known. Especially suited UV absorbing agents, which are effective in the wave length range of 250 to 350 nm, which is of interest here, are benzoic acid derivatives, e.g. p-amino benzoic acid derivatives such as amyl-p-dimethyl amino benzoate and glyceryl-p-amino benzoate or o-hydroxy benzoic acid derivatives; benzophenone derivatives, e.g. 2-hydroxy-4-(2-hydroxy-3-methacryloxy) propoxy benzophenone or 2-hydroxy-4-methoxy benzophenone-5-sulfonic acid; camphor derivatives, coumarin derivatives, benzimidazole derivativs; dibenzoyl methane derivatives; cinnamic acid ester derivatives, e.g. isobutyl cinnamate, ethyl cinnamate or benzyl cinnamate; and tris-(hydroxy methyl) aminomethane salts of a sulfonic acid such as tris-(hydroxy methyl) aminomethane salt of 2-phenyl benzimidazole-5-sulfonic acid.

The UV absorbing agent is preferably used in an amount of 0.001 to 10% by weight, especially preferred of 0.01 to 5% by weight, in particular of 0.03% by weight, based on the composition.

The insecticidal composition used according to the invention is suitably produced in liquid form with the addition of a diluent or solvent. Suited diluents are water, organic solvents or oils, an aqueous and/or oily emulsion being preferred. Monohydric and polyhydric alcohols, glycols such as 1,2-propane diol, and halogenated hydrocarbons can e.g. be used as organic diluents, while saturated and unsaturated ceric acid esters and fatty acid esters, e.g. vegetable oils, and natural and synthetic ethereal oils are especially well suited as oils. In addition, the insecticidal composition may contain lecithin. In practical application, the insecticidal composition can then be sprayed onto the surface to be treated.

The preparation of the insecticidal composition in powder form is carried out in customary fashion by adding a solid carrier such as talcum, zinc and titanium dioxide, calcined magnesia or an anhydrous metal salt.

The insecticidal composition according to the invention can be used against any type of vermin, against which the already known pyrethroid compositions are used, in particular to destroy household vermin such as flies and cockroaches.

I claim:

1. An insecticidal composition comprising from 0.001 to 10% by weight of at least one pyrethroid, an effective amount of at least one UV-absorbing agent and an effective amount of at least one antioxidant, wherein the antioxidant is at least one mono-to tri-ester of citric acid with alkyl alcohols having 1 to 8 carbon atoms.

2. A composition according to claim 1, characterized in that the pyrethroid is pyrethrum.

3. A composition according to claim 1, wherein the UV absorbing agent is a benzoic acid derivative, a benzophenone derivative, a benzoxazole derivative, a camphor derivative, a coumarin derivative, a benzimidazole derivative, a dibenzoylmethane derivative, a cinnamic acid ester derivative or a tris-(hydroxymethyl) aminomethane salt of a 5-sulfonic acid.

4. A composition according to claim 1, characterized in that the UV absorbing agent is a p-aminobenzoic acid derivative.

5. A composition according to claim 1, characterized in that the insecticidal composition contains 0.01 to 2% by weight of the pyrethroid.

6. A composition according to claim 1, characterized in that the insecticidal composition contains 0.01 to 5% by weight of the UV absorbing agent.

7. A composition according to claim 1, characterized in that the insecticidal composition contains 0.001 to 10% by weight of the antioxidant.

8. A composition according to claim 1, characterized in that the insecticidal composition contains 0.01 to 5% by weight of the anti-oxidant.

9. A composition according to claim 1, wherein the insecticidal composition contains ascorbyl palmitate as an additional antioxidant.

10. A composition according to claim 1, wherein the insecticidal composition contains conventional carriers and/or diluents.

11. A composition according to claim 1, characterized in that the insecticidal composition is present in an aqueous or oily emulsion.

12. A composition according to claim 1, characterized in that the insecticidal composition additionally contains lecithin.

13. The composition of claim 1, wherein the pyrethroid is pyrethrum and the UV absorbing agent is a p-aminobenzoic acid derivative.

14. An insecticidal composition comprising from 0.001 to 10% by weight of pyrethrum, an effective amount of a UV absorbing agent of p-aminobenzoic acid derivative, and an effective amount of an ester of citric acid and an alkyl alcohol having 1 to 8 carbon atoms as an antioxidant.

15. The insecticidal composition of claim 14, wherein the citric acid ester is tributyl citrate or acetylbutyl citrate.

16. A method for controlling flying and/or crawling insects comprising contacting said insects with an insecticidally effective amount of the insecticidal composition according to any one of claims 1–15.

* * * * *